US008722095B2

(12) United States Patent
Ibanez et al.

(10) Patent No.: US 8,722,095 B2
(45) Date of Patent: May 13, 2014

(54) FLUORESCENT NANOCRYSTALS ENCAPSULATED IN AN INORGANIC SHELL

(75) Inventors: Alain Ibanez, Voiron (FR); Noélie Marcellin, Grenoble (FR); Elisabeth Djurado, Crolles (FR); Cécile Philippot, Grenoble (FR)

(73) Assignees: Centre National de la Recherche Scientifique—CNRS, Paris (FR); Institut National Polytechnique de Grenoble, Grenoble (FR)

( * ) Notice: Subject to any disclaimer, the term of this patent is extended or adjusted under 35 U.S.C. 154(b) by 351 days.

(21) Appl. No.: 12/933,610

(22) PCT Filed: Mar. 19, 2009

(86) PCT No.: PCT/FR2009/000294
§ 371 (c)(1),
(2), (4) Date: Dec. 13, 2010

(87) PCT Pub. No.: WO2009/125086
PCT Pub. Date: Oct. 15, 2009

(65) Prior Publication Data

US 2011/0110864 A1 May 12, 2011

(30) Foreign Application Priority Data

Mar. 21, 2008 (FR) ..................................... 08 51830

(51) Int. Cl.
*A61K 9/50* (2006.01)
*A61K 9/51* (2006.01)

(52) U.S. Cl.
USPC .......................................... 424/489; 424/490

(58) Field of Classification Search
CPC ................................................... A61K 9/5192
USPC ........................ 424/489, 490, 9.323; 977/777
See application file for complete search history.

(56) References Cited

U.S. PATENT DOCUMENTS

2006/0024436 A1* 2/2006 Bayya et al. .................. 427/212
2007/0269382 A1* 11/2007 Santra et al. ............... 424/9.323

FOREIGN PATENT DOCUMENTS

WO WO 2005015213 A1 * 2/2005

OTHER PUBLICATIONS

Hooisweng Ow et al., "Bright and Stable Core-Shell Fluorescent Silica Nanoparticles", Nano Letters, ACS, Washington, DC, US, vol. 5, No. 1, Jan. 1, 2005, pp. 113-117.

Serge Desportes et al., "Fluorescence lifetime imaging microscopy for in situ observation of the nanocrystallization of rubrene in a microfluidic set-up", Chemical Physics Letters, North-Holland Amsterdam, vol. 446, No. 1-3, Sep. 14, 2007, pp. 212-216.

Virginie Monnier et al., "TEM characterization of organic nanocrystals grown in sol-gel thin films", Journal of nanoparticle Research; An Interdisciplinary Forum for Nanoscale Science and Technology, Kluwer Academic Publishers, DO, vol. 10, No. 1, Apr. 4, 2007, pp. 129-139.

Pirjo Kortesuo et al., "In vitro evaluation of sol-gel processed spray dried silica gel microspheres as carrier in controlled drug delivery", International Journal of Pharmaceutics, vol. 200, 2000, pp. 223-229.

Dan Zhao et al., "Modified spontaneous emission of europium complex nanoclusters embedded in colloidal silica spheres", Chemical Physics Letters, North-Holland, Amsterdam, vol. 403, No. 1-3, Feb. 14, 2005 pp. 129-134.

* cited by examiner

*Primary Examiner* — Michael G Hartley
*Assistant Examiner* — Micah-Paul Young
(74) *Attorney, Agent, or Firm* — Arent Fox LLP

(57) ABSTRACT

The present invention relates to a method of preparing hybrid organo/mineral nanoparticles comprising an organic fluorescent crystalline core encapsulated in an inorganic shell, and to nanoparticles that can be obtained by said method. The method of the present invention comprises the following steps: (i) a sol-gel mixture able to be obtained by a process comprising the addition, in at least one organic solvent, in the presence of water, of a fluorescent organic compound and at least one metal alkoxide is sprayed; (ii) the sprayed sol-gel mixture is dried, by evaporating the solvent and the water that are present in the sol-gel mixture. The nanoparticles of the present invention can be used for example as a tracer in medical imaging or as a chemical sensor.

4 Claims, 5 Drawing Sheets

300 nm

FLUORESCENT NANOCRYSTALS ENCAPSULATED IN AN INORGANIC SHELL

CROSS-REFERENCE TO RELATED APPLICATION

This application is a National Stage entry of International Application No. PCT/FR2009/000294, filed Mar. 19, 2009, which claims priority to French Patent Application No. 08/51830 filed Mar. 21, 2008, the disclosure of the prior application is incorporated in its entirety by reference.

TECHNICAL FIELD

The present invention relates to a process for preparing organomineral hybrid nanoparticles, and also to nanoparticles comprising at least one fluorescent organic nanocrystal coated with an inorganic shell, which may be obtained via said process and may be used, for example, as tracers in imaging or as chemical sensors.

The process of the present invention includes the following steps:

(i) nebulizing a sol-gel mixture which may be obtained via a process including the addition to at least one organic solvent, in the presence of water, of at least one fluorescent organic compound and of at least one metal alkoxide;

(ii) drying the nebulized sol-gel mixture by evaporating off the solvent and the water present in the sol-gel mixture.

In the description below, the references in parentheses (Ref. x) refer to the list of references given after the examples.

PRIOR ART

Optical methods play a major role in clinical research, in particular for the development of diagnostic and prognostic tests or for the development of new therapies. In particular, angiography is a medical imaging technique that is very commonly used for medical diagnosis. Specifically, the study of blood vessels makes it possible to identify vascular pathologies, anomalies associated with blood flow, detect the path of vessels and thus to develop a suitable treatment or to enable optimum preparation for a surgical intervention. In addition, it is a technique that is widely used in neurosciences.

It is generally the fluorescence of an injected dye which, following light excitation, serves to image the blood vessels. The standard protocol consists in simultaneously injecting two dyes, one with a low molecular mass is chosen for its ability to cross the blood-brain barrier (blood vessel walls), whereas the other, with a markedly higher molecular weight, is in contrast intended only for intravascular staining (not diffusible across blood vessel walls).

The desirable properties of the diffusible dye are largely satisfied by a broad range of commercial dyes, which, on the other hand, is not the case for intravascular staining. Specifically, dyes intended for intravascular staining require high molecular weights, but the only existing commercial solution for intravascular staining consists in grafting onto a voluminous polymeric aggregate, such as dextran or albumin, a fluorescent molecule. However, it is difficult to graft a large number of fluorophores onto the same polymeric aggregate. This leads to high dilution of the chromophores, resulting in insufficient imaging contrast during studies of deep blood vessels. Thus, the current techniques make it possible to image shallow blood vessels (about one mm deep) but remain insufficient for a deep examination of the permeable and lesioned capillaries which are generally encountered within tumors.

Specifically, the absorption and diffusion of the excitation light are responsible for this depth limitation. An excitation by laser scanning microscopy in the spectral region 650-1000 nm makes the loss by absorption through bone, dura mata and white and gray matter of the brain negligible.

To overcome the diffusion problem, one solution would be to increase the power of the laser. However, this route, which is generally adopted for ex-vivo imaging, is not tolerable in vivo since it causes local heating that disrupts the measurement and may also cause irreversible legions. For example, a limit value of tolerable in vivo laser power, determined empirically, is a few mW at the focal point of the objective for an excitation wavelength of 800 nm.

Another solution to the depth limitation in imaging consists in using more luminous traces, either by increasing the local concentration of fluorophores, or by using fluorophores with high luminescence yields.

Thus, semiconductive nanocrystals have been developed, as described, for example, in the article by D. R. Larson et al., *Sciences* 300 (2003), 1434-1436 (Ref. 1).

However, semiconductive nanocrystals are difficult to synthesize in large amounts since their synthesis is long, complicated and very expensive. Specifically, the synthesis is performed in several steps: in a first step, it is a matter of obtaining a small fluorescent core, i.e. of 2 to 5 nm maximum. In a second step, it is imperative to form, by hetero-epitaxial growth, a shell of a semiconductor with a larger gap, so as to overcome the blinking problems.

Specifically, blinking problems are caused by surface defects that give rise to transient and random non-fluorescent states. For example, J. S. Steckel et al., *Ang. Chem. Inter. Ed.* 43 (2004), 2154-2158 (Ref. 2) describes nanocrystals obtained by growth of a ZnS shell. Furthermore, these semiconductive nanocrystals are not biocompatible and are not dispersible in physiological saline either. Thus, the synthesis requires a third step that consists in functionalizing these semiconductive nanocrystals, for example by encapsulation in phospholipid micelles as described in the article by B. Dubertret et al., *Sciences* 298 (2002), 1759-1762 (Ref. 3).

Another drawback concerns the loss of efficacy of semiconductive nanocrystals when they are highly excited, due to the interaction between carriers, such as the Auger effect.

Moreover, other fundamental research studies underway relate to the development by sol-gel chemistry in solution of silica particles in which are dispersed or grafted onto the silicate matrix fluorescent organic molecules, as described in the document by Larson et al., *Nano Letters*, vol. 5 (2005), 1, 113-117 (Ref. 4). However, for this type of biological tracer, the concentration of fluorescent molecules remains limited. Furthermore, no benefit is drawn here from the crystalline state of the fluorescent organic part that stabilizes the organic fluorophores all the more chemically and photochemically. The reason for this is that it is not a matter here of nanocrystals of organic fluorophores at the core of the particle.

Many biomedical applications, for instance imaging techniques, require large amounts of fluorophore in order to obtain staining of the entire circulatory system. These techniques are especially of considerable interest for the development of novel therapies for man. These techniques are generally tested in a first stage on mice and rats and require about 10 mg of fluorophore per mouse and much more for rats, which is a serious handicap for semiconductive nanocrystals for simple reasons of cost.

The biomedical applications also require nano-crystals with very narrow size distributions and very good stabilities in order to visualize several times the same in vivo region and to be able to observe changes over time (migration mechanisms of tracers, therapeutic changes, etc.).

There is thus a real need for improved luminescence nanocompounds that can totally or partially solve the problems listed above, especially in terms of stability and resistance, for example thermal, mechanical, chemical, biochemical and/or photochemical resistance.

There is also a real need for luminescent nano-compounds that have good optical properties, such as fluorescence, photostability and transparency range, but also good surface properties, such as roughness, which has an influence on the optical properties or the hydrophilic nature necessary for the biocompatibility or the ability of the compounds to be dispersed in physiological solutions.

In addition, there is a real need for a quick and simple process for preparing these optimized nanocompounds that can be applied to large-scale synthesis and that also make it possible to reduce the manufacturing costs and to improve the yields and the amounts produced.

DESCRIPTION OF THE INVENTION

The aim of the present invention is, precisely, to satisfy these needs and drawbacks of the prior art by providing a process for preparing nanoparticles comprising at least one fluorescent organic nanocrystal coated with an inorganic shell, said process comprising the following steps:

(i) nebulizing a sol-gel mixture that may be obtained via a process comprising the addition to at least one organic solvent, in the presence of water, of at least one fluorescent organic compound and of at least one metal alkoxide of formula (I) below:

$R^1_xM(OR^2)_y$ Formula (I)

in which:

M is a metal chosen from the group comprising Si, Ti, Zr, Sn, B, Al and Y, for example Si;

x is an integer ranging from 0 to 2, for example 0 or 1;

y is an integer ranging from 1 to 6, for example 3 or 4;

x+y corresponds to the coordination number of the metal M;

$R^1$ and $R^2$ independently represent an organic radical that is compatible with sol-gel chemistry;

(ii) drying the nebulized sol-gel mixture by evaporating off the solvent and the water present in the sol-gel mixture.

According to one particular embodiment, the invention relates to a process for preparing nano-particles comprising a fluorescent organic crystalline core coated with an inorganic shell, said process comprising the following steps:

(i) nebulizing a sol-gel mixture that may be obtained via a process comprising the addition to at least one organic solvent, in the presence of water, of a fluorescent organic compound and of at least one metal alkoxide of formula (I) below:

$R^1_xM(OR^2)_y$ Formula (I)

in which:

M is a metal chosen from the group comprising Si, Ti, Zr, Sn, B, Al and Y, for example Si;

x is an integer ranging from 0 to 2, for example 0 or 1;

y is an integer ranging from 1 to 6, for example 3 or 4;

x+y corresponds to the coordination number of the metal M;

$R^1$ and $R^2$ independently represent an organic radical that is compatible with sol-gel chemistry;

(ii) drying the nebulized sol-gel mixture by evaporating off the solvent and the water present in the sol-gel mixture.

Sol-gel chemistry and the various methods for performing it are known to those skilled in the art, have formed the subject of many reports and publications, and will not be developed in the context of the present patent. Mention will be made, for example, of the reference book in the field by C. J. Brinker and G. W. Scherer, Sol-Gel Science, The Physics and Chemistry of SolGel Processing, Academic Press, New York, 1990 (Ref. 5), the article by Avnir et al., *J. Non. Cryst. Solids,* 1985, 74, 395-406 (Ref. 6) or Sanchez et al., *New J. Chem.,* 1994, 18, 1007-1047 (Ref. 7).

A person skilled in the art may select $R^1$ and $R^2$ in the light of the abovementioned publications and of his general knowledge in the field of sol-gel chemistry. For example, $R^1$ and $R^2$ may independently represent a $C_1$ to $C_{15}$ alkyl, $C_1$ to $C_{15}$ heteroalkyl, $C_6$ to $C_{25}$ aryl or $C_4$ to $C_{25}$ heteroaryl radical, the radicals $R^1$ and $R^2$ being optionally independently substituted with one or more groups R independently chosen from the group comprising a $C_1$ to $C_{10}$ alkyl, $C_1$ to $C_{10}$ hetero-alkyl; $C_6$ to $C_{10}$ aryl or $C_4$ to $C_{10}$ heteroaryl radical; F; Cl; Br; I; $—NO_2$; —CN; or a function $-GR^{G1}$ in which G is —O—, —S—, $—NR^{G2}—$, —C(═O)—, —C(═O)O—, —C(═O)$NR^{G2}—$, in which each occurrence of $R^{G1}$, $R^{G2}$ and $R^{G3}$ is, independently of the other occurrences of $R^{G1}$, a hydrogen atom or a $C_1$ to $C_{10}$ alkyl, $C_1$ to $C_{10}$ heteroalkyl; $C_6$ to $C_{10}$ aryl or $C_4$ to $C_{10}$ heteroaryl radical; or alternatively, when G represents $—NR^{G2}—$, $R^{G1}$ and $R^{G2}$ together with the nitrogen atom to which they are attached form an optionally substituted heterocycle or heteroaryl.

For the purposes of the present invention, the term "alkyl" radical means a linear or branched, cyclic or acyclic, saturated or unsaturated carbon-based radical. It may be, for example, $C_{1-15}$alkane; $C_{2-15}$alkene; $C_{2-15}$alkyne; $C_{3-15}$cycloalkyl. According to the invention, the alkyl radical may comprise 1 to 15 carbon atoms, for example 1 to 10 carbon atoms, for example 1 to 6 carbon atoms. For the purposes of the present invention, the term "heteroalkyl" means an alkyl radical, as defined previously, in which at least one carbon atom is replaced with a heteroatom, chosen especially from the group comprising oxygen, sulfur, nitrogen, phosphorus and boron. It may be, for example, a heteroalkane, a heteroalkene, a heteroalkyne, a heterocycle, an alkoxy, an alkylthio, an alkylamine, an alkylamide, an alkylimine, an alkylimide, an alkyl ester, an alkyl ether, etc. According to the invention, the heteroalkyl radical may comprise 1 to 15 carbon atoms, for example 1 to 10 carbon atoms, for example 1 to 6 carbon atoms.

For the purposes of the present invention, the term "aryl" means a radical comprising at least one ring that satisfies the Hückel aromaticity rule. Said aryl may be monocyclic or polycyclic, and fused or unfused. It may be, for example, a phenyl, a benzyl, a tolyl, etc. According to the invention, the aryl radical may comprise 6 to 25 carbon atoms, for example 6 to 18 carbon atoms, for example 6 to 10 carbon atoms. For the purposes of the present invention, the term "heteroaryl" means an aryl radical, as defined previously, in which at least one carbon atom is replaced with a heteroatom, chosen especially from the group comprising oxygen, sulfur and nitrogen.

For the purposes of the present invention, the term "sol-gel" mixture means a mixture initially comprising at least one metal alkoxide of formula (I) in the presence of water, at least one organic solvent and at least one fluorescent organic compound, said mixture being initially in the form of a solution and producing a gel by hydrolysis and polycondensation reaction. Specifically, the presence of water makes it possible to initiate hydrolysis and condensation reactions of the metal alkoxides forming an inorganic network leading to gels and then to xerogels. These xerogels lead to a structured inorganic solid network of metal oxides. Sol-gel chemistry is cited, for example, in patent FR 2 853 307 (Ref. 8).

Once the sol-gel mixture has been made, the following hydrolysis (1) and condensation (2) reactions of the metal alkoxides may take place, for example, leading to "inorganic polymers" of metal oxides:

$$R^1_xM\ (OR^2)_yH_2O \rightarrow R^1_x(OR^2)_{y-1}M(OH)+HOR^2 \quad (1)$$

$$R^1_x(OR^2)_{y-1}M\ (OH)+R^1_x(OR^2)_{y-1}M(OH) \rightarrow R^1_x(OR^2)_{y-1}M\text{-}O\text{-}M(OR^2)_{y-1}R^1_x+H_2O \quad (2)$$

in which $R^1$, $R^2$, x and y are as defined previously.

Advantageously, the sol-gel mixture of the process of the invention may be homogeneous and chemically and mechanically stable. For example, it may be stable for several months or even several years, which is a great advantage for the industrial development of the process of the invention.

For the purposes of the present invention, the term "metal alkoxides", also known as "sol-gel precursors", means any metal compound of formula (I). According to the invention, any metal alkoxide known to those skilled in the art may be used provided that an interconnected polymeric sol-gel network may be obtained. The reader may refer, for example, to the reference book by C. J. Brinker and G. W. Scherer, Sol-Gel Science, The Physics and Chemistry of SolGel Processing, Academic Press, New York, 1990. (Ref. 5).

For the purposes of the present invention, the term "fluorescent organic compound", also known as a "fluorophore", means any organic compound known to those skilled in the art which is fluorescent in the crystalline state. Optionally, the fluorescent organic compound may be initially introduced in the form of microcrystalline powder, and totally dissolved in the solvent in order to obtain a solution that is entirely homogeneous at the molecular level.

According to the invention, the fluorescent organic compound may be chosen, for example, from the group comprising the polyaromatic family, for example rubrene or tetracene, the stilbene family, for example cyano-methoxy-nitro-stilbene (CMONS) or diethyl-amino-nitro-stilbene, the naphthalimide family, the rhodamine family, for example rhodamine B, the diarylmethane family, for example auramine O, the perylene diimide family, boron dipyrromethene difluoride derivatives, rare-earth metal complexes, for example ruthenium, osmium, iridium, europium, ytterbium, erbium or neodymium complexes. In one particular embodiment, the organic compound may be rubrene or CMONS.

For the purposes of the present invention, the term "fluorescent" compound or nanocrystal means a compound or nanocrystal that has the property of emitting, following light excitation, electromagnetic radiation in the field of visible light or in the near infrared (IR). For example, the fluorescent compound or nanocrystal may emit electromagnetic radiation at wavelengths of 400 to 1200 nm, which corresponds to the window of relative transparency of living tissues. For example, the fluorescent compound or nanocrystal may emit electromagnetic radiation at wavelengths of 400 to 1000 nm, for example from 550 to 800 nm, which corresponds to fluorescence in the red and near infrared region. Specifically, in these wavelength ranges, biological tissues are the most transparent, which constitutes an advantage for applications in imaging.

For the purposes of the present invention, the term "solvent" means any solvent known to those skilled in the art which is compatible with the sol-gel process of the present invention, i.e. which can make the metal alkoxides and the water of hydrolysis miscible so as to obtain homogeneous solutions that are sparingly viscous so that they can be nebulized. Advantageously, the solvent allows the fluorophore to be totally dissolved.

According to the invention, the solvent present in the sol-gel mixture may be initially introduced in a large amount relative to the initial amount of metal alkoxide. For example, the sol-gel mixture may initially comprise a number of moles of solvent 20 to 200 times higher than the initial number of moles of metal alkoxide, preferably 50 to 100 times higher.

According to the invention, the water present in the sol-gel mixture may be initially introduced in a small amount, this amount being sufficient to initiate the reactions leading to polycondensation of the inorganic network, or in an amount larger than the initial amount of metal alkoxide. For example, the sol-gel mixture may initially comprise a mole percentage of water relative to the number of alkoxide functions (—$OR^2$) of 10% to 400%, preferably from 20% to 100% and more preferably from 50% to 100%.

According to the invention, the sol-gel mixture may initially comprise a number of moles of fluorophore 100 to 5 times lower than the initial number of moles of metal alkoxide, preferably 20 to 10 times lower.

According to one particular embodiment of the invention, the process of the invention may make it possible to prepare nanoparticles comprising at least one fluorescent organic nanocrystal coated with an inorganic shell, said at least one nanocrystal not emerging at the surface of the shell.

According to another embodiment of the invention, said nanoparticle may comprise a single fluorescent organic nanocrystal coated with an inorganic shell.

The process of the present invention may also comprise, before the nebulization step (i), a preliminary step (0) of preparing the sol-gel mixture to be nebulized. Step (0) of preparing the sol-gel mixture may comprise:

a step (0a) of preparing an initial mixture, for example by mixing in a solvent at least one fluorescent organic compound and at least one metal alkoxide in the presence of water; and optionally, a step (0b) of storing the initial mixture for a time d in order to allow the initial mixture to react.

According to the invention, the time d may be less than several months or even several years. For example, the time d may be from 1 day to 1 year, for example from 7 days to 21 days. Specifically, storage of the mixture allows the mixture to be matured in order to advance the hydrolysis and condensation reactions of the metal alkoxides.

According to the invention, step (0) of preparing the sol-gel mixture to be nebulized may comprise the addition of an acid to the initial mixture. Specifically, by lowering the pH of the mixture, the acid makes it possible to promote the production of long inorganic chains that are favorable to the formation of a dense inorganic shell around the organic crystals. According to the invention, the pH of the mixture may be from 1 to 7, preferably from 1 to 2.

For the purposes of the present invention, the term "acid" means mineral or organic Bronsted acids. Among the acids that may be used, examples that may be mentioned include hydrochloric acid, nitric acid and acetic acid.

According to one particular embodiment of the invention, the process of the present invention may be performed with one or more of the following conditions:

(a) the fluorescent organic compound may be chosen, for example, from the group comprising the polyaromatic family, the stilbene family, the naphthalimide family, the rhodamine family, the diarylmethane family, the perylene diimide family, boron dipyrromethene difluoride derivatives, and rare-earth metal complexes;

(b) the metal alkoxide may be chosen, for example, from the group comprising tetramethoxysilane (TMOS, $Si(OCH_3)_4$), tetraethoxysilane (TEOS, $Si(OC_2H_5)_4$), methyltrimethoxysilane (MTMOS, $CH_3Si(OCH_3)_3$), ethyltriethoxysilane (ETEOS, $C_2H_5Si(OC_2H_5)_3$) 1,2-bis(trimethoxysilyl)ethane (TMSE), 3-glycidoxypropyl)trimethoxysilane (GPTMS), or a mixture thereof;

(c) the solvent may be chosen, for example, from the group comprising the alcohols $R^S$—OH in which $R^S$ is a $C_1$ to $C_6$ alkyl radical, the ketones $R^{S1}$—C(═O)—$R^{S2}$, the ethers $R^{S1}$—$R^{S2}$, in which $R^{S1}$ and $R^{S2}$ are independently $C_1$ to $C_6$ alkyl radicals, tetrahydro-furan, acetonitrile, dimethylformamide, toluene, dimethyl sufoxide, dioxane, acetone, acetic acid, formic acid, dichloromethane, chloroform, dichloroethane, ethyl acetate, diethyl ether or a mixture thereof.

According to one more particular embodiment of the invention, the fluorescent organic compound may be chosen from the group comprising rubrene, tetracene, cyano-methoxy-nitro-stilbene (CMONS), diethylamino-nitro-stilbene, rhodamine B, auramine O and europium, ytterbium, erbium or neodymium complexes.

According to the invention, step (i) of nebulizing the sol-gel mixture may be performed under vacuum or under an atmosphere of a gas so as to generate an aerosol from the sol-gel mixture. The nebulization step (i) may be performed, for example, by ultrasonication, by pneumatic nebulization, by electro-spray, by injection, by nozzles of ink-jet printer type, etc. Preferably, step (i) of nebulizing the sol-gel mixture may be performed by ultrasonication, for example by piezoelectric excitation of the solution. Specifically, this technique has the advantage of generating aerosols formed from droplets with narrow size distributions.

The process of the present invention may also comprise, after step (i) and before step (ii), a step (iii) of transporting the aerosol in a stream of gas to a drying area of a reactor, step (ii) being performed in said drying area. Advantageously, the gas used is a dry, dust-free gas. In all the embodiments described in the present invention, among the dry gases that may be used (for example for the transportation and/or drying of the aerosol), examples that may be mentioned include air, nitrogen, argon, helium and $CO_2$. Advantageously, step (iii) of transporting the aerosol may be performed in a laminar flow so as to reduce the coalescence of the droplets.

According to the invention, step (ii) of drying the sol-gel mixture consists in evaporating the solvent and the water present in the sol-gel mixture. The water present in the mixture may be the water introduced in step (0) and/or produced during the polycondensation reactions of the metal alkoxides. The acid optionally added to the mixture during step (0) may also be evaporated off during step (ii). According to the invention, step (ii) of drying the nebulized sol-gel mixture makes it possible, by evaporating off the solvent and the water contained in the droplets, to form the inorganic network by polycondensation, leading firstly to the formation of the inorganic shell at the periphery and at the end of evaporation of the solvent to organic crystallization at the core of the nanoparticle. Specifically, at the start of evaporation of the solvent, the formation of an "inorganic skin" is denser at the surface of the droplet than deeper down since the evaporation of the solvent is higher at the periphery of the drop. Next, as the evaporation of the solvent continues, supersaturation of the organic phase very rapidly increases in the residual solvent, while the probability of nucleation becomes markedly higher at the core of the drops than at their surface. Specifically, this probability of nucleation $dP_N$ is directly proportional to the volume of the pores of the inorganic network undergoing polycondensation: $dP_N$=J.V.dt, in which J is the degree of nucleation (in nuclei per second), V is the volume in which nucleation takes place (in $cm^3$) and dt is the time interval (in seconds). The nucleation of the organic nanocrystals thus takes place at the center of the drops where the volume of the pores and the probability of nucleation are higher. During the end of evaporation of the solvent, the growth of the organic nanocrystals pushes the sol-gel network that is not yet very rigid toward the periphery. Thus, after total removal of the solvent, hybrid particles formed from an organic nanocrystalline core coated with a dense, amorphous inorganic shell are obtained. This initial hypothesis, of confined growth of nanocrystals at the core of the inorganic particle during densification, has been confirmed by various characterization techniques, some of which are presented in the examples below.

Advantageously, the drying step (ii) may be performed rapidly, for example in a time of less than 1 minute, for example from 1 to 60 seconds and preferably from 10 to 20 seconds. Specifically, rapid drying makes it possible to avoid coalescence of the drops. However, an overly instantaneous evaporation of the solvent (less than one second) leads to poor crystallinity of the organic core.

According to the invention, the drying step (ii) may be performed with at least one of the following conditions:

with temperature and pressure conditions allowing the evaporation of the solvent and the water present in the sol-gel mixture;

under a stream of dry gas;

in the presence of a material that can uptake the at least one solvent.

The temperature and pressure conditions may also optionally allow the evaporation of the acid that may be present in the sol-gel mixture.

The temperature and pressure conditions that may be used depend on the boiling point of the solvent or solvent mixture used. In addition, the temperature conditions must be lower than the degradation temperature of the organic nanocrystals. For example, the drying step (ii) may be performed at a temperature below 300° C., preferably from 50 to 150° C. In addition, the drying step (ii) may be performed under vacuum, under reduced pressure or in an atmosphere of dry gas. For example, the drying step (ii) may be performed by raising the temperature coupled with dilution in a dry gas.

The term "material capable of taking up the at least one solvent" means an absorbent, adsorbent or drying material. Said material may, for example, be arranged around a porous tube in which circulates the aerosol undergoing drying. Among the materials that may be used, examples that may be mentioned include active charcoals for trapping organic solvents.

The process of the present invention may also comprise, after step (ii), a step (iv) of collecting the nanoparticles at the outlet of the drying area. For example, the collecting step (iv) may be performed using a glass plate, a screen, a filter, a porous membrane, a filter cartridge combined with a pump. The mode of collection of the particles may be optimized, for example, by using at the end of the reactor an electrostatic filter that consists in collecting particles charged under high tension. Specifically, such a filter makes it possible to pass the particles between two electrodes subjected to a high potential difference (of several kV). The particles that become charged on one of the electrodes may thus be harvested. This mode of collection with an electrostatic filter is described, for example, for the collection of yttrium oxide nanoparticles in the document by Joffin et al., *J. of Luminescence* 113 (2005), 249-257 (Ref. 9). Another collection method may be a filter cartridge combined with a pump (for example a membrane pump) so as to create a negative pressure at the reactor outlet, just after the drying area, and to recover with the aid of a filter cartridge the particles after drying. By optimizing these two particle collection systems, the yield of the process may reach values close to 100%. This second route should promote laminar flow of the aerosol and thus reduce the coalescence of the drops that entrains broadening of the particle size distribution. According to one particular embodiment of the invention, the collecting step (iv) also makes it possible to select particular sizes of nanoparticles.

The process of the present invention thus leads to nanoparticles with an organic phase at the center and an inorganic phase at the periphery. In other words, they are nanoparticles of core-shell geometry, in which the core is formed from a crystalline fluorescent organic compound ("crystalline core") and the shell is in an inorganic layer. For the purposes of the present invention, the term "organic phase" means the part of the nanoparticle constituting the fluorescent nanocrystal confined at the center. For the purposes of the present invention, the term "inorganic phase" means the part of the nanoparticle constituting the inorganic shell.

Thus, the preparation process of the invention allows the production of pure, very luminous hybrid nanoparticles, of uniform size distribution. This process is a very simple and mild method since it is performed at a temperature close to room temperature. Specifically, the production of the nanoparticles is performed in a single reaction step starting with stable, homogeneous solutions that are easy to prepare. Furthermore, this method is generic since it is applicable to any soluble organic fluorophore that can be recrystallized in the organic solvent that is compatible with the sol-gel process.

In addition, the preparation process of the invention has the advantage of allowing these nanoparticles to be obtained in large amount and continuously, in a limited number of steps, with high yields and a low production cost. For example, the preparation process of the invention allows these nanoparticles to be obtained in a yield of at least 25%, for example at least 50%, for example greater than 70%, for example greater than 80%, for example greater than 90%, for example close to 100%. Thus, the process of the invention is directly transposable to the industrial level.

Furthermore, the process of the present invention readily allows the size of the nanoparticles to be modulated, which has an impact on their furtivity in a biological medium (in particular, sizes less than 80-100 nm are favorable for the use of these nanoparticles as tracers in imaging) and enables the study of migration of medicaments in vivo. Specifically, the size of the particles may be governed, for example, by the size of the droplets formed in the aerosol and above all more easily by the proportion of organic solvent relative to the amounts of fluorophores and of alkoxide of the initial mixture. Furthermore, the more the sol-gel precursors and the fluorophore are diluted in the solvent, the smaller the size of the particles obtained after drying.

The process of the invention also makes it possible to control the thickness of the shell or the size of the nanocrystal so as to optimize the optical properties as a function of the envisioned type of application, for example cerebral angiography.

In particular, the inventors have demonstrated the main experimental parameters (mole ratios of metal alkoxides, solvent, organic chromaphore and water, formation of aerosol and drying conditions, etc.) for controlling the nanocrystallization conditions, i.e. the nucleation and confined growth of the organic molecules within the sol-gel matrix. Controlling the nanocrystallization conditions leads to a good nanocrystal diameter/hybrid particle diameter ratio, by modifying the alkoxide/organic phase relative proportion. According to one particular embodiment of the invention, the nanocrystal diameter/nanoparticle diameter ratio may be greater than 0.5.

In addition, this production method requires perfect control of the aerosol with narrow size distributions of droplets, transportation under laminar flows of the aerosol so as to minimize the coalescence of the droplets, etc. To do this, various types of solution nebulization reactors may be used depending on the desired nebulization method (for example ultra-sonication, pneumatic, electrospray, nozzles of ink-jet printer type as mentioned previously).

The invention also relates to a nanoparticle comprising at least one fluorescent organic nanocrystal coated with an inorganic shell, said at least one nanocrystal not emerging at the surface of the shell.

According to one particular embodiment, said nanoparticle may be obtained according to the process of the invention. These novel fluorescent nanocompounds may be used, for example, as tracers or chemical sensors.

According to one particular embodiment of the invention, said nanoparticle comprises a fluorescent organic crystalline core coated with an inorganic shell (i.e. a "core-shell" nanoparticle). As it is a nanoparticle, the crystalline core is of nanometric size (i.e. a size necessarily less than the size of the nanoparticles defined below). In other words, it is a nanocrystal.

They may be referred to as nanoparticles with a "pure" crystalline core, as opposed to the nanoparticles reported by Larson et al., for example, the core of which is formed from fluorescent organic molecules dispersed in or grafted to a silicate matrix (Ref. 4). The "pure" crystalline core of the nanoparticles of the invention allows better photo-stability and luminosity.

According to a more particular embodiment, the crystalline core of the nanoparticle according to the invention may be monocrystalline. Specifically, surprisingly, the process of the present invention makes it possible to obtain nanoparticles comprising a monocrystalline core, i.e. a core formed from a single homogeneous crystal, whose reticular planes have a uniform orientation throughout the volume of the crystal. The monocrystallinity of the core of the nanoparticles of the invention gives them unique fluorescence emission behavior and makes it possible to envision novel applications of the nanoparticles as ultra-sensitive sensors or as sensors with a very high contrast of fluorescence intensity as a function of the chemical or biological environment. Specifically, in the case of monocrystals, the unique emission behavior is very advantageous for performing the signaling function of sensors (which have only two states: one corresponding to zero intensity (0), the other in which the nanocrystal is fluorescent (1 detection)). Conversely, nanoparticles form from a polycrystalline core (i.e. formed from several nanocrystals) do not have any unique emission nature, but this will be dependent on the environment. This is reflected by the fluorescence of some of the nanocrystals while the others remain switched off depending on the conditions, and thus by changes in fluorescence intensity rather than quite distinct and easily detectable behaviors (state "0" or "1"), which leads to a very substantial loss of contrast and of sensitivity as a function of the chemical or biological environment.

For the purposes of the present invention, the term "nanoparticle" means a particle of nanometric size. For example, the nanoparticle of the present invention may have a diameter of less than or equal to 1 μm. For example, the nanoparticle may have a diameter ranging from 20 nm (nanometers) to 1

μm, for example from 20 to 800 nm, for example from 20 to 600 nm, for example from 20 to 200 nm, for example from 20 to 100 nm.

Advantageously, the nanoparticle of the present invention may be perfectly spherical. Specifically, the spherical geometry and the good surface properties of the nanoparticles of the present invention, especially in terms of very low surface roughness (of the order of 0.1 to 0.5 nanometers) and of hydrophilicity, improve their optical properties, in addition to promoting their biocompatibility and their conveyance in the biological medium.

For the purposes of the present invention, the term "nanocrystal" means a crystal of nanometric size comprising at least one fluorescent organic compound defined previously. For example, the nanocrystal according to the invention may have a diameter of less than or equal to 1 μm. For example, the nanocrystal may have a diameter ranging from 10 nm to 1 μm, for example from 20 to 700 nm, for example from 20 to 500 nm, for example from 20 to 400 nm, for example from 20 to 300 nm, for example from 10 nm to 200 nm, for example from 10 nm to 100 nm. Specifically, the inventors have been able to develop nanocrystals with a diameter of several tens of nm encapsulated in inorganic spheres with relatively narrow particle size distributions.

Nanocrystals greater than 10 nm in size have the advantage of preventing the particles from being diffusible across blood vessels, especially of mice. The nanocrystal is also referred to as an "organic crystallite" in the present text. It is understood that since the nanocrystal is coated with an inorganic shell in order to constitute the nanoparticle, the size of the nanocrystal is necessarily less than that defined for the above nanoparticles.

Since the nanocrystal is at the core of the nanoparticle, reference may be made to the "crystalline core" to denote the nanocrystal. The two terms are used interchangeably in the present patent application.

The fluorescent crystalline core (or nano-crystal) of the present invention may comprise a plurality of fluorophore molecules. Preferably, the nanocrystal according to the invention may comprise a large number of fluorophore molecules that give it a highly fluorescent organic core. The number of molecules included in the nanocrystal depends on the size of the molecules and on the size of the nanocrystal. According to the invention, the nanocrystal may comprise up to $10^{10}$ fluorophore molecules, preferably up to $10^8$, for example from $10^3$ to $10^8$ molecules, for example from $10^4$ to $10^7$, for example from $10^4$ to $10^6$ fluorophore molecules.

According to the present invention, the term "inorganic shell" means a metal oxide shell. According to the invention, the inorganic shell may be chosen from the group comprising a silicate, titanate, zirconate, stannate, borate, aluminate or yttriate shell. The inorganic shell makes it possible to prevent the organic crystallites from coming into direct contact with the external medium. In addition, it has the advantage of being inert, biocompatible in vivo and of making the nanoparticle of the present invention more furtive. Specifically, the inorganic shell gives the nanoparticle a crucial hydrophilic nature, especially for applications in medical imaging. Furthermore, the shell makes it possible readily to modulate the hydrophilic-hydrophobic balance of the hybrid nanoparticle and thus to adjust its interactions in the body. Specifically, a highly hydrophilic nature facilitates the dispersion of these particles in physiological solutions and their injection into the bloodstream. This pronounced hydrophilic nature significantly reduces in vivo all interactions of these nanoparticles with proteins, making it possible in this case to obtain "furtive" luminous tracers. Conversely, it may also be envisioned to reduce the hydrophilic nature of the inorganic shell by using metal alkoxides (or sol-gel precursors) that have an organic function, for example a non-hydrolysable methyl ($—CH_3$) or ethyl ($—C_2H_5$) group and that will thus be present at the surface of the particles. This less pronounced hydrophilic nature will allow interactions between tracers and certain proteins, which may be revealed.

According to one particular embodiment of the invention, the inorganic shell may be a silicate shell. The silicate shell has the advantage of being inert, amorphous, biocompatible and transparent in the visible and near infrared region. This transparency in the visible and near IR region is favorable for applications in imaging. Furthermore, it is possible to produce non-porous silicate shells.

According to the invention, the inorganic shell be may porous or non-porous.

According to one particular embodiment of the invention, the inorganic shell may be porous. For example, the inorganic shell may be microporous or may have pore sizes of less than 5 nm, preferably less than 2 nm. This allows interactions between the fluorescent nanocrystal and the environment (spent waters, biological media) and the detection of small molecules that are capable of passing through the pores of the shell. This detection is based on a significant variation in the luminescence properties and is applicable, for example, in the field of chemical sensors.

According to another embodiment of the invention, the inorganic shell may be non-porous and thus totally leaktight. Specifically, a non-porous shell has the advantage of chemically stabilizing the fluorescent nanocrystal contained at the core of the shell by preventing any reaction of the fluorophores with the external medium, for example with oxygen, leading to improved photostability. In addition, the crystalline form of the fluorophores contained in the nanocrystal also makes it possible to improve the photostability of the nanoparticles of the present invention.

According to the invention, the inorganic shell may allow light to pass through at visible and IR wavelengths, i.e. from 400 to 3000 nm minimum which thus largely covers the wavelength range of fluorescence of the organic nanocrystals. Specifically, the inorganic shell is made of a metal oxide and is transparent in the visible and near infrared range irrespective of the metal. Thus, this transparency is entirely suited to the intended applications.

According to the invention, the inorganic shell may have a thickness ranging from a few nm to 1 μm. The inorganic shell may, for example, have a thickness ranging from 1 nm to 1 μm and more particularly from 1 to 200 nm, which is more favorable for applications in imaging, for example from 2 to 100 nm.

Thus, the nanoparticles of the present invention have the advantage of being very luminous and non-diffusible across the walls of blood vessels (which is an essential property for angiography) since they comprise a very large number of fluorophore molecules. Specifically, this considerably increases the effective cross section for absorption and thus the fluorescence intensity of these nanoparticles (or the intensity of the radiation emitted by the fluorescent nanocrystal). Thus, by significantly increasing the local concentration of fluorophores in blood vessels, this novel type of tracer makes it possible to obtain fluorescence intensities that are markedly higher than those obtained with the current commercial solutions in which each particle corresponds to a single fluorescent molecule. This gain in intensity is of several orders of magnitude in effective cross section for absorption of the nanocrystals relative to a fluorescent molecule, for example from 2 to 3 orders of magnitude by virtue of this fluorophore concentration effect. This gain is thus liable to lead to a large improvement in image contrast and makes it possible to markedly increase the depth accessible by medical imaging, especially via the laser-scanning biphotonic fluorescence microscopy technique. It may thus be hoped to produce cerebral angiographies for tissue depths that are markedly greater than a centimeter instead of the current 1 mm depth.

Furthermore, the nanoparticles of the present invention have the advantage of being photostable. On the one hand, the sol-gel shell mechanically and chemically stabilizes the organic nanocrystals. On the other hand, the crystallinity of the organic fluoro-phores gives them markedly higher photostability than that generally observed for organic molecules in solution. In addition, the excitations are more localized in the case of organic crystals than in the case of semiconductive crystals, which makes it possible to prevent the loss of efficacy due to the interaction between carriers (for instance the Auger effect). These good photostabilities make it possible in intra-vital imaging to observe the same area several times over time, to observe therapeutic changes or to study the migration of particles of different sizes in these cells or tumors in order to understand the efficacy of nanomedicaments (medicaments encapsulated in biodegradable polymers of “cyanoacrylate” type, for example).

Moreover, the nanoparticles of the present invention are entirely spherical, which gives them very good surface properties, especially in terms of very low surface roughness and hydrophilicity, leading to markedly improved furtivity properties. In particular, unlike the nanoparticles of the prior art that are generally irregular polyhedral of spherical overall shape, the perfectly spherical nature of the particles of the present invention promotes the in vivo furtivity of the nanoparticles, for example for their use as tracers. This allows, for example, better diffusion of the nanoparticles in blood vessels and prevents accumulation of the nanoparticles in certain organs (for instance the liver or the kidneys).

In addition, the nanoparticles of the present invention have the advantage of being biocompatible, hydrophilic and dispersible in physiological solution. Furthermore, their size may be readily modulated, possibly ranging from a few tens to a few hundred nanometers. For example, hydrophilic particles less than about 100 nm in size have the advantage of being only sparingly perturbed or not perturbed by proteins. Specifically, proteins interact in vivo and may adhere to any foreign particle and entrain it to a specific organ that is not generally the tumor that it is desired to characterize. In addition, the study of the influence of the size of tracers on their capacity for access and migration in tumors will make it possible to better understand the efficacy of certain medical treatments.

Thus, these organomineral hybrid nanomaterials combine the advantages of organic nanocrystals (high luminescence intensity, photostability, size effects, etc.) with those of the amorphous mineral matrix (stability, ease of forming and transparency).

The invention also relates to the use of nano-particles according to the invention as tracers in medical imaging. Specifically, the particular characteristics of the nanoparticles of the present invention, especially in terms of increased luminosity, improved photostability, biocompatibility, controlled size, make them very luminous tracers for medical imaging. The applications may concern man or animals, including small animals. For example, laser cerebral angiography is used on small animals (rats or mice) in order to test the novel therapies under development for man. Specifically, deep angiography of the cerebral cortex of mice makes it possible to test medicaments and novel therapies under development and also diagnostic methods under development in man, for instance laser ocular angiography.

Thus, according to one particular embodiment of the invention, the medical imaging may be, for example, cerebral angiography or ocular angiography. In particular, the use of the nanoparticles of the present invention excited by two-photon transition may lead to better, deeper cerebral angiography, with a lower laser power and fewer chromophores injected since they are concentrated in the form of crystallites endowed with a totally biocompatible shell. This makes it possible to reduce or eliminate the trauma generally caused by examinations of this type.

The synthesis of the nanoparticles according to the invention has the advantage of being simple and generic, performed in a single reaction step, and makes it possible to produce different tracers by using different organic phases that are fluorescent at different wavelengths or active in quadratic nonlinear optics (noncentrosymmetrical nanocrystals). Thus, this method has the advantage of selecting fluorophores that are adapted to a particular type of application, for example of selecting fluorophores that emit in the red region so as to benefit from the good transparency of biological tissues in this wavelength range.

According to one particular embodiment of the invention, the invention also relates to the use of nanoparticles according to the invention as chemical sensors. Specifically, the inorganic shell of a nano-particle according to the invention may allow, as a function of its porosity and of the size of its pores, the passage of molecules present in the medium in which the nanoparticle is placed. Thus, the porous inorganic shell of a nanoparticle according to the invention may allow interactions between the fluorescent nanocrystal and the molecules of the external medium. These interactions may give rise to a significant variation in the luminescence properties, which allows the detection of the molecules of the external medium. As an example of implementation for the use of nanoparticles as chemical sensors, an example that may be mentioned is the document by Burns et al., *Small,* vol. 2 (2006), 723-726 (Ref. 10), which describes silica beads comprising fluorescent organic molecules functioning as pH sensors. However, the synthesis of these beads does not lead to crystallization of the fluorescent phase. The crystalline core of the nanoparticle of the present invention has the advantage of containing a larger number of fluorescent organic molecules (as described previously). This high number of molecules leads to very high effective cross sections for absorption and thus to very high fluorescence intensities. The interactions of the crystalline core of the nanoparticle of the invention with molecules of the external medium may thus give rise to large variations in fluorescence, leading to the production of very efficient chemical sensors. For the use of the nanoparticles of the invention as chemical sensors, the crystalline core may comprise any fluorescent organic molecule or rare-earth metal complex having very high fluorescence intensities excited with two photons is usable (for instance the abovementioned fluorophores).

Other advantages may also appear to a person skilled in the art on reading the examples below, illustrated by the attached figures, which are given as illustrations.

EXAMPLES

Example 1

Synthesis of Rubrene Nanocrystals Coated with a Silicate Shell

In this example, rubrene is chosen for the production of organic nanocrystals included in silica spheres. Rubrene has orange-red luminescence (wavelength band from 550 to 600 nm) for which biological tissues show good transparency.

Figure 1:
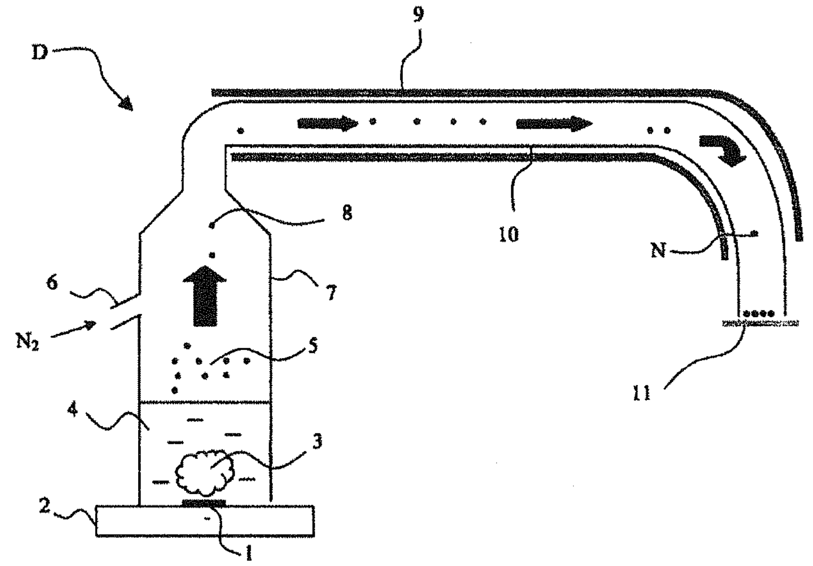
FIG. 1 is a device D for implementing the process of the invention and for obtaining the nanoparticles (N) of the invention. In the scheme, (1) represents a piezoelectric ceramic for exciting the solution, (2) represents the base of the reactor and (3) represents the cavitation phenomenon caused by the ultrasonication. The solution (4) is nebulized as an aerosol (5) formed from droplets (8). The inlet (6) allows the circulation of the gas that entrains the droplets (8) to a drying area (10) surrounded by a heating resistance (9). The nanoparticles (N) are then collected by means of a glass plate (11).

The synthesis of the nanoparticles of the present invention according to the process of the present invention is illustrated by FIG. 1 which represents the reactor (7) comprising a sol-gel mixture (4). The sol-gel mixture (4), after nebulization, leads to the aerosol (5) formed from droplets (8). The gas inlet (6) allows transfer of the aerosol to the area (10) for drying the aerosol surrounded with a heating resistance (9). Once dried, the nanoparticles (N) of the invention are collected by means of a glass plate (11).

Procedure for Preparing the Sol-Gel Mixture (4):

The microcrystalline rubrene powder (0.18 g; 3.3 mmol; sold by the company Aldrich) was dissolved in a solution containing 138.75 mL of tetrahydrofuran, 4.16 mL (1.5 mmol) of tetramethoxysilane (TMOS) and 4.03 mL (1.5 mmol) of methyltrimethoxysilane (MTMOS).

Water and HCl were introduced simultaneously in the form of a dilute 0.1 M hydrochloric acid solution of volume 3.56 mL. The water activates the hydrolysis and polycondensation reactions of the silicon alkoxides, leading, after evaporation of the THF, to the formation of the silicate shell. After the addition of this acidic solution, the pH of the mixture is about 1.

The solution was then stored for 1 month in order to advance the hydrolysis and condensation reactions of the alkoxides.

Nebulization of the Sol-Gel Mixture (4) and Drying:

The homogeneous and stable solution (4) was then atomized by ultrasonication in order to obtain an aerosol (5) formed from droplets (8) with narrow size distributions (FIG. 1). The nebulization was performed using a piezoelectric nebulization reactor (sold by the craft company RBI, France) operating at a frequency of 2.1 MHz to nebulize the solution (4) with droplet sizes of about 2 microns (μm).

The aerosol was then transported in a stream of nitrogen (2-3 L/min) to a hot area (10) (at a temperature of 150° C.) in order rapidly to evaporate the organic solvent and to initiate in each droplet the polymerization of the silicate network.

The nanoparticles (N) were collected at the outlet of the drying area (10) of the reactor directly on glass slides (11) arranged perpendicular to the stream of nitrogen transporting the aerosol (FIG. 1). The glass slides rapidly turned whitish because of the deposition of the silicate particles.

0.53 gram of nanoparticles was thus obtained (which corresponds to a yield of about 25%). This low yield is due to the inefficient method of collecting the particles (at the outlet of the drying area on glass slides).

The invention is described hereinabove by way of example. It is understood that a person skilled in the art is capable of using different means for performing the invention without, however, departing from the context of the invention. In addition, in one embodiment, not illustrated, the particles may be collected using an electrostatic filter (Joffin et al., *J. of Luminescence* 113 (2005) 249-257 (Ref. 9)). It may also be envisioned to draw under vacuum and to recover the particles after drying using a filter cartridge. By optimizing these two systems for collecting particles, the yield for the process may reach levels close to 100%.

Characterization:

After the synthesis, the nanoparticles of the present invention may be characterized according to various techniques.

Figure 2:
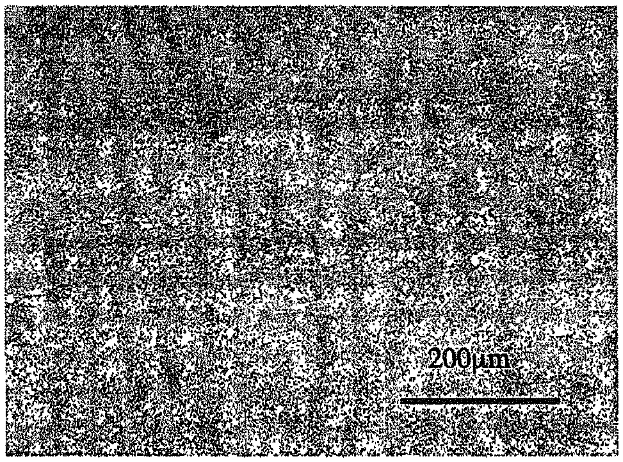
FIG. 2 represents the visualization by optical microscopy of the nanoparticles collected on glass slides according to Example 1.

Firstly, a macroscopic characterization was performed by standard optical microscopy and fluorescence optical microscopy in order to specify the overall homogeneity of the particles of the synthesis. The images obtained by optical microscopy confirmed the presence of white submicron particles, of uniform appearance, without any segregation of the silicate and organic phases (FIG. 2). Furthermore, under UV exposure, the white deposit of particles became orange-red, very homogeneous in intensity, which confirms the homogeneity of the organomineral hybrid particles.

Figure 3:
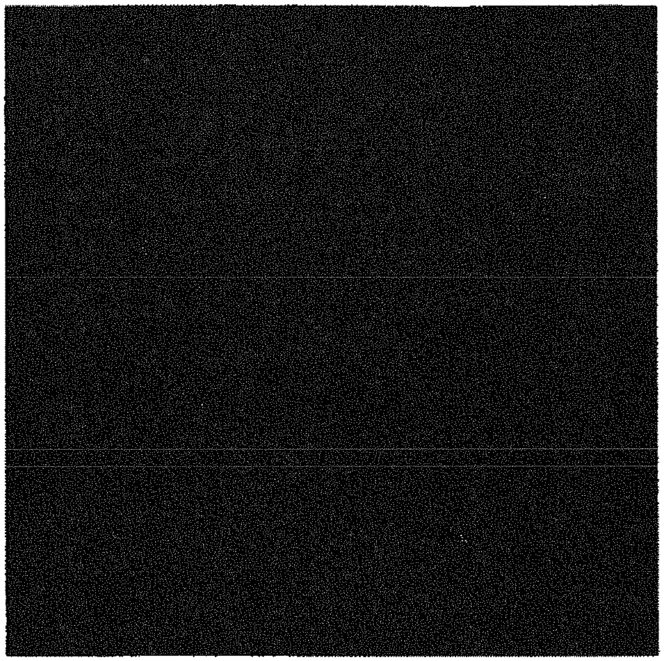
FIG. 3 represents the two superposed images in confocal optical microscopy of the same area of glass slide comprising nanoparticles obtained according to Example 1: one of the images is obtained in reflection mode, and the other in fluorescence mode.

Next, the particles adhered to the surface of the glass slide were then observed by confocal optical microscopy in reflection and fluorescence modes. In reflection mode, particles of the order of a few hundred nm in size are observed, which appear to be spherical despite the optical distortions (interference) that slightly deform the images and a few air bubbles trapped in the refractive index fluid used for this optical microscopy. In fluorescence mode, it is observed that all these particles become luminescent. FIG. 3 represents the superposition of the two confocal optical microscopy images, one obtained in reflection mode and the other recorded in fluorescent mode. They indeed confirm that all the particles observed are fluorescent with very high intensities given the large number of rubrene molecules contained in these isolated particles.

Figure 4:
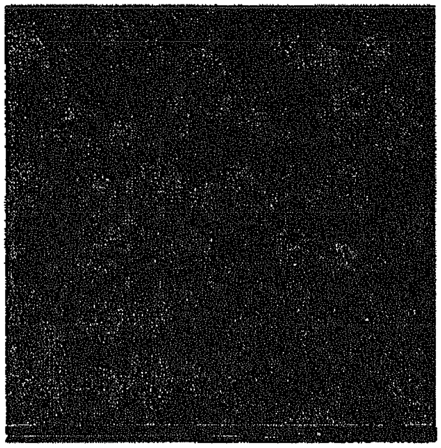
FIG. 4 represents nanoparticles obtained according to Example 1 observed by SEM (Scanning Electron Microscopy), with sizes of between 100 and 600 nm in diameter.

The nanoparticles obtained were then analyzed by scanning electron microscopy (SEM, FIG. 4) in order to specify the size and size distribution of the particles. Perfectly spherical particles are observed, with a broad size distribution between 100 and 600 nm but with a large majority of particles at about 400 to 500 nm due to the first nanocrystallization conditions, which remain to be perfected:

transportation of the aerosol in a laminar flow in order to reduce the coalescence of the droplets, higher solvent content to reduce the particle size, optimization of an area for faster drying of the aerosol (temperature, controlled atmosphere, etc.), improvement of the conditions for recovering the particles (electrostatic filter, filter cartridges+pump, etc.).

Figure 6:
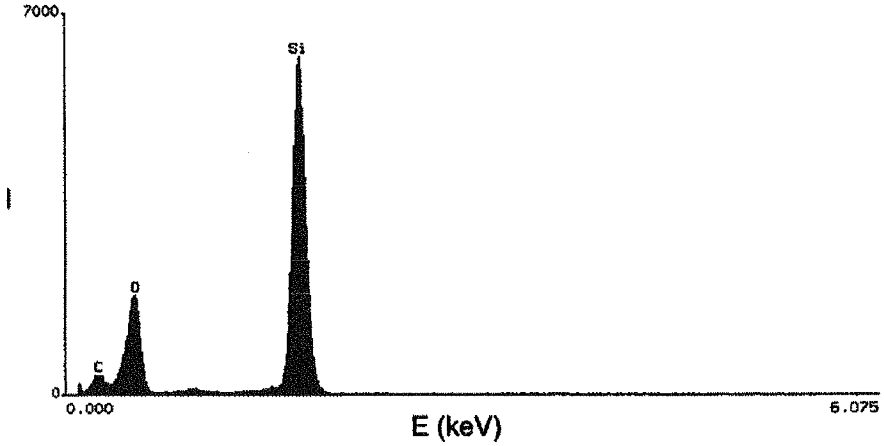
FIG. 6 represents the EDS (Energy Dispersive Spectroscopy) chemical analysis performed on the organosilicate hybrid nanoparticles obtained according to Example 1. The intensity I of the lines observed is represented as a function of the energy E of the recorded RX radiations (in keV).

The EDS (Energy Dispersive Spectroscopy) chemical analysis was performed on the organosilicate hybrid nanoparticles obtained according to Example 1 and is shown in FIG. 6 with, on the X-axis, the energy of the recorded X rays (E in keV) and, on the Y-axis, the intensity of each line (I as counts recorded on the detector). The K lines (alpha) characteristic of Si and O atoms corresponding to the silicate shell, and the K line (alpha) of carbon corresponding to the core of the particle (organic rubrene nanocrystal) are observed. Thus, the chemical analysis by EDS with SEM clearly confirms the presence of a silicate shell and made it possible to observe the presence of the elements Si, O and C, which confirms the production of organosilicate hybrid nanoparticles.

Figure 5:
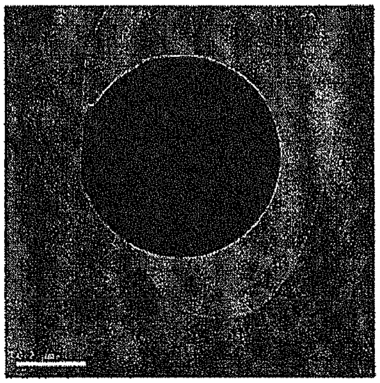
FIG. 5 represents a nanoparticle obtained according to Example 1 observed by TEM (Transmission Electron Microscopy).

Finally, the hybrid nanoparticles were characterized by transmission electron microscopy (TEM). The first TEM observations (FIG. 5) confirm the perfectly spherical form of the nanoparticle, and the size observed previously on SEM. This visualization clearly shows the sphericity of the particles obtained via this process with very low roughness of a few angstroms (0.1 to 0.5 nm) of the inorganic shell that is at the surface of the particle. The flat area to the left of the particle (in black in FIG. 5) corresponds to the contact of the nanoparticle during drying with the glass slide that served to recover the particles during the first tests. More rigorous drying and a more appropriate collection method (electrostatic filter or filter cartridge) may make it possible to avoid any type of defect and thus to obtain totally spherical particles.

Figure 7:
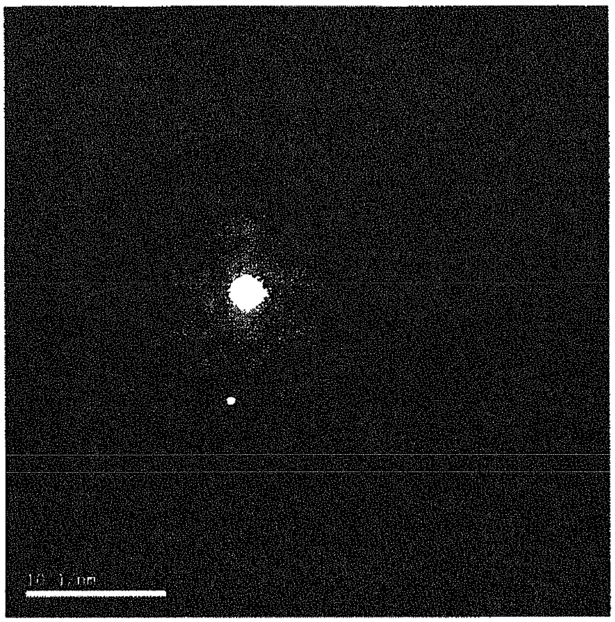
FIG. 7 is an electron diffraction image recorded at room temperature on a nanoparticle.

Next, the crystallinity and the structure of the nanocrystals located at the core of the hybrid particles were characterized by transmission electron microscopy in diffraction mode. The inventors recently mastered a TEM electron diffraction technique of "low dose" type that makes it possible to work with a small electron current and at low temperature (liquid $N_2$) in order substantially to reduce the degradation of the organic nanocrystals under the electron beam. Specifically, the first recordings were perturbed by the degradation of the nanocrystals under the focused electron beam in diffraction mode. This evanescent behavior is typical of the degradation of organic nanocrystals, as the inventors have already observed during the study of nanocrystals in thin layers as described in the document from A. Ibanez et al., *J. Nanoparticle Research* 10 (2008), 129-139 (Ref. 11). The first diffraction tests nevertheless made it possible to record, at a low electron current, several images at room temperature and to prove the good crystallinity of the organic nanocrystals: FIG. 7 is an electron diffraction image recorded at room temperature on a nanoparticle. This clearly proves the presence of the crystalline organic core (nanocrystal). Specifically, via the sol-gel process used, only amorphous silicates are formed, which do not produce any diffraction phenomenon. These first diffraction images are noteworthy since it is the first time that electron diffraction spots have been able to be observed at room temperature for organic nanocrystals. These first diffractograms are thus very encouraging since they demonstrate the good monocrystallinity of the organic nanocrystals (a single nanocrystal per nanoparticle). Specifically, only one diffraction diagram is observed for each particle, formed from very focused spots. Furthermore, the size of these nanocrystals is greater than 40 nm in diameter, which is very encouraging for the production of highly luminous tracers formed from a high number of chromophores. Lowering the temperature makes it possible to record more diffraction spots, to correctly exploit their relative intensities and to characterize more finely the structure and crystallinity of these spots.

This mean size of the organic nanocrystals, located at the core of the nanoparticles, may be determined more precisely by testing several types of characterization techniques such as high-resolution X-ray diffraction (broad lines) for small particles and also inelastic light scattering X-ray diffusion. High-resolution X-ray diffraction is an essential measurement and is complementary to electron microscopies (SEM and TEM) which make it possible to visualize only all of the hybrid particles (organic core and silicate shell). This necessitates good control of the nanocrystallization conditions leading to a good nanocrystal diameter/hybrid particle diameter ratio. The nanoparticles of the present invention may also be characterized by small-angle X-ray diffusion and by inelastic light scattering.

Example 2

Synthesis of Cyano-Methoxy-Nitro-Stilbene (CMONS) Nanocrystals Coated with a Titanium Oxide Shell The procedure of Example 1 is repeated with, in this example, a sol-gel mixture (4) prepared from:

0.65 g (i.e. 2.32 mmol) of cyano-methoxy-nitro-stilbene (CMONS);

140 mL (i.e. 1.7 mol) of tetrahydrofuran (THF) solvent;

10.06 mL (i.e. $3.3\times10^{-2}$ mol) of titanium iso-propoxide as sol-gel precursor;

2.46 mL of a solution of hydrochloric acid in water (of concentration 0.1 M), i.e. 0.14 mol of water.

After nebulization of the sol-gel mixture and drying of the aerosol according to the method described in Example 1, the titanate nanoparticles are collected in a yield of about 30% by mass of nanoparticles.

Example 3

Synthesis of Cyano-Methoxy-Nitro-Stilbene (CMONS) Nanocrystals Coated with a Silicate Shell In this example, the conditions for synthesizing the nanoparticles according to the invention are as follows:

the silicate matrix is formed from 50% of tetra-methoxysilane (TMOS, $Si(OCH_3)_4$) and 50% of methyl-trimethoxysilane (MTMOS, $CH_3Si(OCH_3)_3$), the amount of chromophore (CMONS) used for the synthesis (or ratio of the concentration of CMONS to the concentration of silicon alkoxide) is d=[CMONS]/[silicon alkoxide]=0.05, the degree of dilution (ratio of the concentration of solvent to the concentration of silicon alkoxide) is s=[solvent]/[silicon alkoxide]=50, the acid catalysis is performed at a pH below 2, the degree of hydrolysis (ratio of the concentration of water to the concentration of alkoxide functions (—$OR^2$) originating from the metal alkoxides TMOS and MTMOS) is $h=[H_2O]/[—OR^2]=1$ (the concentrations are calculated on the basis of the initial mixture, in other words the process is performed here with as many water molecules as alkoxide functions (—$OR^2$) of the compound of formula (I)), the solvent used is THF, the total volume of the solution is set at 240 mL a) Preparation of the Sol-Gel Mixture:

The procedure of Example 1 for the preparation of the sol-gel mixture was performed with the following proportions:

780.4 mg of α-[(4'-methoxyphenyl)methylene]-4-nitro-benzeneacetonitrile (or CMONS);

228.4 mL of THF (tetrahydrofuran) solvent;

4.112 mL of tetramethoxysilane (TMOS) and 3.976 mL of methyltrimethoxysilane (MTMOS) as sol-gel precursors;

3.512 mL of a solution of hydrochloric acid in water (of concentration 0.1 M).

This solution was then placed in an oven at 50° C. for 4.5 days to start the hydrolysis and the condensation of the alkoxides (TMOS and MTMOS). Next, it was stored at room temperature (from 15 to 25° C.) for 20 days protected from light so as to mature the solution (i.e. to advance the hydrolysis and condensation reactions of the alkoxides).

After maturation, the mixture was vaporized by pneumatic nebulization.

b) Synthesis of the Nanoparticles by Pneumatic Nebulization:

The above sol-gel mixture was sprayed by pneumatic nebulization in which the mixture is fragmented under pressure of a gas arriving perpendicularly by a nozzle, allowing the production of an aerosol formed from droplets with a size of about 1 to 2 microns. The nebulization was performed for 4 hours using a pneumatic nebulization reactor (model 3076 atomizer sold by the company TSI Inc., USA) with the following nebulization parameters:

oven temperature: $T_{oven}=150°$ C.;

temperature of the electrostatic filter: $T_{electrostatic\ filter}=140°$ C.

gas (dinitrogen) pressure: $P_{N2}=1.8$ bar;

flow rate of compressed air (in liters per hour): $D_{compressed\ air}=2.5$ L/h.

The aerosol was then transported in a gas stream and dried according to the method described in Example 1. The collection of the nanoparticles is performed at the outlet of the drying area by means of an electrostatic filter, performed by applying a voltage of 10 kV (kilovolts). Thus, 2.2 grams of nanoparticles were obtained (which corresponds to a yield of about 50%). By optimizing the conditions and the collection of the particles, the yield for the process can reach values close to 100%.

c) Separation of the Particles by Centrifugation:

The nanoparticle powder obtained after nebulization is polydisperse. The coarse particles are thus then separated from the fines by centrifugation.

To do this, 15 mg of powder were placed in 30 mL of demineralized water. The solution was then sonicated so as to disperse the powder in the water. Next, centrifugation was performed.

The centrifugation was performed for 30 seconds at 7800 rpm to separate the coarsest particles (800-1000 nm). These are thus “layered” at the bottom of the collected tube.

The supernatant was recovered in order to recentrifuge it for 5 minutes at 5000 rpm so as to obtain this time the medium-sized particles (400-700 nm). These particles are thus found at the bottom of the collected tube.

The various flasks of particles obtained were then treated separately so as to expose the core of the nanoparticles of the invention, enabling its monocrystallinity to be demonstrated.

d) Demonstration of the Monocrystalline Single Core:

in the case of nanoparticles obtained by pneumatic nebulization, with a diameter of 800 nm to 1 micron These nanoparticles (15 mg) were then introduced into 20 mL of a $10^{-2}$M NaOH solution and the whole was stirred magnetically for one week at room temperature (15 to 25° C.), leading to pure crystalline particles of CMONS.

Figure 8:
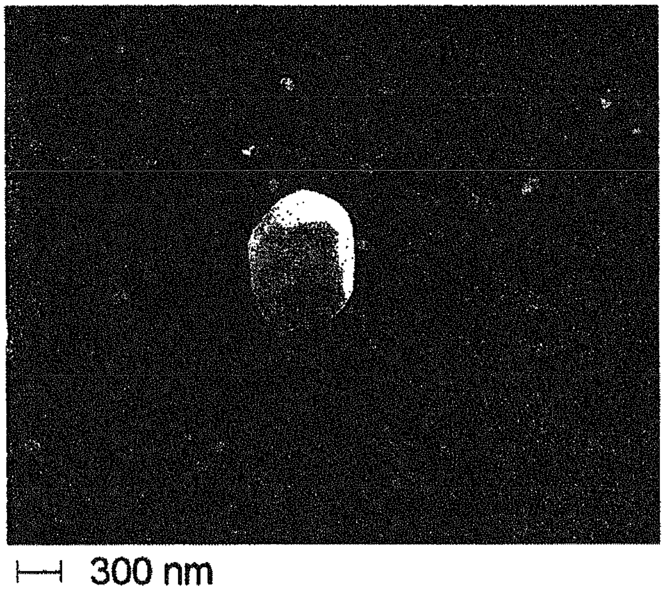
FIG. 8 represents a microcrystalline core, obtained from a nanoparticle of about 1 micron, freed of its shell (obtained by pneumatic nebulization and then dissolution of the shell according to Example 3) observed by SEM (Scanning Electron Microscopy). The cores obtained have sizes of about 500 to 600 nm in diameter.

In this manner, it was demonstrated that the nanoparticles comprising a CMONS core coated with a silicate shell according to the invention are formed from a single pure nanocrystal of CMONS and that this nanocrystal is monocrystalline. The SEM analysis of the CMONS nanocrystals shows that these monocrystals have a diameter of about 500 to 600 nm (FIG. 8).

in the case of nanoparticles obtained by pneumatic nebulization, with a diameter of 400 nm to 700 nm These nanoparticles (20 mg) were then introduced into 40 mL of a $10^{-3}$M NaOH solution and the whole was stirred magnetically for three weeks at room temperature (15 to 25° C.), leading to pure crystalline particles of CMONS.

Figure 9:
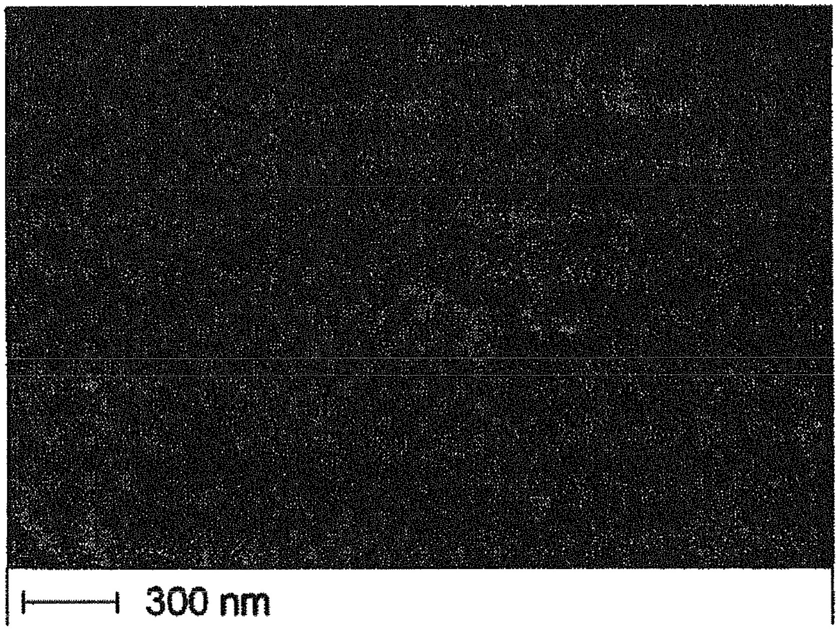
FIG. 9 represents a nanocrystalline core, obtained from a nanoparticle of about 500 nm, freed of its shell (obtained by pneumatic nebulization and then dissolution of the shell according to Example 3) observed by SEM (Scanning Electron Microscopy). The cores obtained have sizes of about 200 to 300 nm in diameter.

In this manner, it was demonstrated that the nanoparticles comprising a CMONS core coated with a silicate shell according to the invention are formed from a single pure nanocrystal of CMONS and that this nanocrystal is monocrystalline. The SEM analysis of the CMONS nanocrystals shows that these monocrystals have a diameter of about 200 to 300 nm (FIG. 9).

LIST OF REFERENCES (1) “Water-soluble quantum dots for multiphonon fluorescence imaging in vivo” D. R. Larson et al., *Sciences* 300 (2003), 1434-1436.

(2) “Blue luminescence from (CdS)ZnS core-shell nanocrystals” J. S. Steckel et al., *Ang. Chem. Inter. Ed.* 43 (2004), 2154-2158.

(3) “In vivo imaging of quantum dots encapsulated in phospholipids micelles” B. Dubertret et al., *Sciences* 298 (2002), 1759-1762.

(4) “Bright and stable Core-shell fluorescent silica nanoparticles” H. Ow, D. R. Larson, M. Srivastava, B. A. Baird, W. W. Webb, U. Wiesner. *Nano Letters, vol.* 5, No. 1, 113-117 (2005).

(5) C. J. Brinker and G. W. Scherer, *Sol-Gel Science,* The Physics and Chemistry of SolGel Processing, Academic Press, New York, 1990.

(6) Avnir D., Kaufman V. R., Reisfeld R., *J. Non. Cryst. Solids,* 1985, 74, 395-406.

(7) C. Sanchez and F. Ribot, *New J. Chem.,* 1994, 18, 1007-1047.

(8) Patent FR No. 2 853 307

(9) N. Joffin, J. Dexpert-Ghys, M. Verelst, G. Baret, A. Garcia, *J. of Luminescence* 113 (2005) 249-257

(10) A. Burns, P. Sengupta, T. Zedayko, B. Baird and U. Wiesner, *Small*, Vol. 2 (2006), 723-726.

(11) “TEM characterization of organic nanocrystals grown in sol-gel thin films”. A. Ibanez et al., *J. Nanoparticle Research* 10 (2008), 129-139.

The invention claimed is:

1. A process for preparing nanoparticles comprising a fluorescent organic nanocrystal core coated with an inorganic shell, said process comprising the following steps:

(i) nebulizing a homogenous sol-gel mixture that is obtained via a process comprising the addition of at least one organic solvent, in the presence of water, of at least one fluorescent organic compound and of at least one metal alkoxide of formula (I) below:

$R^1_xM(OR^2)_y$ Formula (I)

in which:

M is a metal chosen from the group comprising Si, Ti, Zr, Sn, B, Al and Y;

x is an integer ranging from 0 to 2;

y is an integer ranging from 1 to 6;

$R^1$ and $R^2$ independently represent an organic radical that is compatible with sol-gel chemistry;

(ii) drying the nebulized homogenous sol-gel mixture by evaporating off the solvent and the water present in the homogenous sol-gel mixture.

2. The process as claimed in claim 1, performed with at least one of the following conditions:

(a) the fluorescent organic compound is chosen from the group comprising the polyaromatic family, the stilbene family, the naphthalimide family, the rhodamine family, the diarylmethane family, the perylene diimide family, boron dipyrromethene difluoride derivatives, and rare-earth metal complexes;

(b) the metal alkoxide is chosen from the group comprising tetramethoxysilane (TMOS, $Si(OCH_3)_4$), tetraethoxysilane (TEOS, $Si(OC_2H_5)_4$), methyltrimethoxysilane (MTMOS, $CH_3Si(OCH_3)_3$), ethyltriethoxysilane (ETEOS, $C_2H_5Si(OC_2H_5)_3$), 1,2-bis(trimethoxysily) ethane (TMSE), 3-glycidoxypropyl)trimethoxysilane (GPTMS), or a mixture thereof;

(c) the solvent is chosen from the group comprising the alcohols $R^s$—OH in which $R^s$ is a $C_1$ to $C_6$ alkyl radical, the ketones $R^{S1}$—C(═O)—$R^{s2}$, the ethers $R^{S1}$—O—$R^{S2}$, in which $R^{S1}$ and $R^{S2}$ are independently $C_1$ to $C_6$ alkyl radicals, tetrahydrofuran, acetonitrile, dimethylformamide, toluene, dimethyl sufoxide, dioxane, acetone, acetic acid, formic acid, dichloromethane, chloroform, dichloroethane, ethyl acetate, diethyl ether or a mixture thereof.

3. The process as claimed in claim 1, in which the fluorescent organic compound is chosen from the group comprising rubrene, tetracene, cyano-methoxy-nitro-stilbene (CMONS), diethylamino-nitro-stilbene, rhodamine B, auramine O and europium, ytterbium, erbium and neodymium complexes.

4. The process as claimed in any one of claims 1 to 3, in which the drying step (ii) is performed with at least one of the following conditions:

with temperature and pressure conditions allowing the evaporation of the solvent and the water present in the homogenous sol-gel mixture;

under a stream of dry gas;

in the presence of a material that can uptake the at least one solvent.

* * * * *